(12) United States Patent
Aarts et al.

(10) Patent No.: US 9,445,750 B2
(45) Date of Patent: Sep. 20, 2016

(54) HEART RATE MEASURING DEVICE

(75) Inventors: Ronaldus Maria Aarts, Eindhoven (NL); Sidarto Bambang Oetomo, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 884 days.

(21) Appl. No.: 13/318,362

(22) PCT Filed: May 6, 2010

(86) PCT No.: PCT/IB2010/051998
§ 371 (c)(1),
(2), (4) Date: Nov. 1, 2011

(87) PCT Pub. No.: WO2010/133996
PCT Pub. Date: Nov. 25, 2010

(65) Prior Publication Data
US 2012/0053471 A1    Mar. 1, 2012

(30) Foreign Application Priority Data
May 18, 2009 (EP) .................................... 09160455

(51) Int. Cl.
*A61B 5/0205* (2006.01)
*A61B 5/11* (2006.01)
*A61B 5/00* (2006.01)

(52) U.S. Cl.
CPC ............ *A61B 5/1102* (2013.01); *A61B 5/6891* (2013.01); *A61B 2503/04* (2013.01)

(58) Field of Classification Search
CPC ...... A61B 5/02; A61B 5/024; A61B 5/0402; A61B 5/11; A61B 5/1102
USPC ........................................ 600/508, 509, 527
See application file for complete search history.

(56) References Cited

U.S. PATENT DOCUMENTS

| | | | | |
|---|---|---|---|---|
| 3,949,246 A | * | 4/1976 | Lohrmann | 310/332 |
| 4,320,766 A | * | 3/1982 | Alihanka et al. | 600/484 |
| 4,474,185 A | * | 10/1984 | Diamond | 600/535 |
| 4,679,569 A | * | 7/1987 | Lee | 600/527 |
| 4,884,578 A | | 12/1989 | Morgenstern | |
| 5,448,996 A | | 9/1995 | Bellin et al. | |
| 5,479,939 A | | 1/1996 | Ogino | |
| 7,048,697 B1 | | 5/2006 | Mitsuru | |
| 2005/0027320 A1 | * | 2/2005 | Nehls et al. | 607/9 |

(Continued)

FOREIGN PATENT DOCUMENTS

| | | | | |
|---|---|---|---|---|
| EP | WO 2008/111002 | * | 9/2008 | A61B 5/11 |
| JP | H0428345 A | | 1/1992 | |

(Continued)

*Primary Examiner* — Amanda Patton

(57) ABSTRACT

The invention relates to a heart rate measuring apparatus and a method, adapted for measuring a subject's (6) heart rate and/or heart rate variation. The heart rate measuring apparatus (1) comprises a holder (2) adapted for carrying a portion of a body part of the subject (6) lying on or resting against the holder (2), a motion sensor (4) operatively connected to the holder (2), wherein the holder (2) is adapted for being at least partly moveable in a horizontal direction relative to the ground (7), the motion sensor (4) being adapted for measuring a signal generated by a movement of the subject (6) at least partly in the horizontal direction. In this way, a reliable signal is obtained adapted for measuring the heart rate and/or heart rate variation of a subject while keeping the implementation costs low.

22 Claims, 1 Drawing Sheet

(56) References Cited

U.S. PATENT DOCUMENTS

| | | |
|---|---|---|
| 2005/0215915 A1 | 9/2005 | Noda et al. |
| 2006/0270941 A1 | 11/2006 | Xie et al. |
| 2008/0039730 A1 | 2/2008 | Pu et al. |
| 2008/0077020 A1 | 3/2008 | Young et al. |
| 2011/0060250 A1* | 3/2011 | Yanaga .................. 600/587 |

FOREIGN PATENT DOCUMENTS

| | | | |
|---|---|---|---|
| JP | 2002219108 A | 8/2002 | |
| JP | 2004170163 A | 6/2004 | |
| JP | 2008183181 A | 8/2008 | |
| WO | 2008111002 A2 | 9/2008 | |
| WO | WO 2008/111002 * | 9/2008 | ............... A61B 5/11 |

* cited by examiner

HEART RATE MEASURING DEVICE

FIELD OF THE INVENTION

The invention relates to the field of heart rate measuring, and especially to measuring the heart rate and/or the heart rate variability in an unobtrusive way.

BACKGROUND OF THE INVENTION

Document US 2008/0077020 A1 describes a method and an apparatus for monitoring vital signs, such as cardiopulmonary activity, using a ballistograph. The method and the apparatus are used to monitor an infant sleeping in a crib, a patient in a hospital, a person with a chronic disease at home or in professional care, or a person in an elder-care setting.

Heart activity is one of the most important vital life signs for a human or an animal. In the following, a subject comprises a human, such as a baby or a neonate, and an animal. In this description, neonates are focused on. However, the idea of the invention is applicable to all humans or animals. The heart rate, HR for short, and also the heart rate variation or heart rate variability, HRV for short, have become a topic of interest in physiology and in psychology. Both values are of particular interest to monitor vital life signs. HRV is attributed to the balance between the para-sympathetic nervous system and the sympathetic nervous system, PNS and SNS for short, respectively decreasing and increasing the HR.

The principle of a ballistographic method is based on a motion sensor, placed or positioned under a mattress of a lying person for monitoring the movements of that person, in particular in the vertical direction relative to the fixed ground.

However, the use of the ballistographic method is problematic due to the fact that such a method mainly measures forces oriented in a vertical direction relative to the ground. However, the force due to the aortic arch impulse in a subject's body, preferably a human's body, is mainly oriented in a horizontal direction relative to the ground.

Besides the ballistographic method, the use of electrodes is known as well. This alternative of measuring heart activity by electrodes is obtrusive, in particular for the neonate, the baby or the child, because the child must be easily forwarded to its parents in order to improve the parent child contact or the child must be easily accessible for care givers, for instance for doctors or nurses working in a hospital. It goes without saying that the skin of the child is very thin and fragile, and may be damaged by removing the electrodes. On the other hand, such a system is robust and able to detect HR among disturbing movement artifacts and the system is for hygienic reasons easy to maintain.

Nevertheless, there is a need for overcoming the problems of the prior art, in particular when measuring HR or HRV of neonates.

SUMMARY OF THE INVENTION

It is the object of the invention to provide a possibility to measure the heart rate and/or the heart rate variation of a subject in a reliable and non-obtrusive way while keeping the implementation costs low.

This object is achieved by the subject matter of the independent claims. Preferred embodiments are defined in the sub claims.

According to a first aspect of the invention, this object is achieved by a heart rate measuring apparatus, adapted for measuring a subject's heart rate and/or heart rate variation, comprising a holder adapted for carrying a portion of a body part of the subject lying on or resting against the holder, and a motion sensor operatively connected to the holder, wherein the holder is adapted for being at least partly moveable in a horizontal direction relative to the ground, and the motion sensor is adapted for measuring a signal generated by a movement of the subject at least partly in the horizontal direction.

It is an idea of the invention, to sense or measure the force of the aortic arch impulse in a horizontal direction relative to the ground or relative to the longitudinal direction of the subject rather than in the vertical direction using a motion sensor. Therefore, a ballistograph is applied in a new fashion adapted for obtaining a reliable signal from which information about heart activity, such as HR and/or HRV, is extractable.

It is noted that the term "a body part" refers a part of the corpus of the subject, like the complete body, the upper part of the body and/or a limb of the subject. The subject can be a human, such as a neonate, or an animal. The term "movement of the subject" refers to the movement of the body part, such as the movement of the complete body, the chest and/or a limb.

The feature that the motion sensor is adapted for measuring a signal generated by a movement of the subject at least partly in the horizontal direction means that the movement is at least measured in a direction horizontal to the ground on which the holder is placed, wherein the movement—additional to its component in a horizontal direction—may also comprise components in a vertical direction relative to the ground. Therefore, also a combined horizontal and vertical movement can be measured and is subject to the present invention.

Measuring a signal generated by a movement of the subject with a horizontal component is advantageous since—for a lying person—the force due to the aortic arch impulse is typically oriented in the horizontal direction relative to the ground and relative to the longitudinal axis of the holder, respectively.

Preferably, the motion sensor corresponds to one of an electrical motion sensor, such as an accelerometer, a mechanical motion sensor and an optical motion sensor.

According to a preferred embodiment of the invention, the heart rate measuring apparatus further comprises a monitoring unit operatively connected to the motion sensor, wherein the monitoring unit is adapted for receiving the signal from the motion sensor and is adapted for generating from the signal, information about the subject's heart rate and/or heart rate variation. Preferably, the monitoring unit is adapted for relaying the information about the subject's heart rate and/or heart rate variation to a user. The monitoring unit preferably comprises a display unit adapted for displaying the information about HR and/or HRV.

It is worth noting that the term "relaying the information about the subject's heart rate and/or heart rate variation to a user" means that a user, such as the subject itself or a person different from the subject, such as a doctor or a nurse, is informed about the state of HR and/or HRV by watching a display unit, comprised by the monitoring unit, which is adapted for displaying the information.

According to another preferred embodiment of the invention, the motion sensor corresponds to an electrical motion sensor comprising a capacitor with an electrical capacitance formed between a first electrode and a second electrode, the first electrode being fixed relative to the ground and the second electrode being fixed relative to the holder.

A change in electrical capacitance is preferably determined by the relative position between the first electrode and the second electrode, the change being proportional to a rate equal to HR and/or HRV. Preferably, the output signal of the heart rate measuring apparatus comprises a signal with a frequency proportional to HR and/or HRV. According to a further preferred embodiment of the invention, the capacitor is comprised by an oscillator circuit, the output of which is a frequency signal modulated by the heart rate. Preferably, the oscillator's output is a binary signal. In this way, the output is directly in the digital domain and no analog-to-digital converter (ADC) is required. The ballistographic signal is obtained by detecting the frequency modulation, and by determining its frequency, the heart rate is obtained. If the output is not a binary signal, the heart rate measuring apparatus preferably comprises an analog-digital converter, which is adapted for converting an analog output signal to a digital output signal, preferably to a binary output signal.

According to yet another preferred embodiment of the invention, the heart rate measuring apparatus further comprises a scale adapted for determining the force and/or weight of the subject in a direction at least partly perpendicular to the ground. According to a further preferred embodiment, a suspension unit is provided which is adapted for allowing a movement of the holder at least partly in the horizontal direction. Preferably, the holder comprises a bed, a mattress, a cushion, a crib and/or an incubator, and the suspension unit preferably comprises a spring.

According to a second aspect of the invention, this object is achieved by the use of the heart rate measuring apparatus according to the first aspect of the invention, wherein the HR and/or the HRV is measured, preferably for monitoring applications, and/or the HR and/or the HRV are used for determining the occurrence of a heart failure, wherein preferably, upon determination of the heart failure, the heart rate measuring apparatus generates an alarm signal.

According to a third aspect of the invention, this object is achieved by a method, adapted for measuring a subject's heart rate and/or heart rate variation, comprising the step of measuring a signal generated by a movement of the subject at least partly in a horizontal direction relative to the ground.

Preferably, a capacitive measuring system is used due to its reliability and low implementation costs. Preferably, the capacitive measuring system is intended to measure human heart activity, in particular heart activity of neonates lying in an incubator. The capacitive measuring system is easily combinable with a scale adapted for determining a baby's or neonate's weight.

The inventive heart rate measuring apparatus can easily built in or be embedded in an incubator, such as a neonatal intensive care incubator. Measuring the HR without using sensors attached to or positioned close to the subject's body is preferred. It goes without saying that this is less obtrusive, in particular for neonates which lie in a neonatal intensive care incubator.

For example, the method can be used to determine the HR or HRV during sleep of a subject, or during sleep onset, or to detect sleep pathologies, e.g. restless legs syndrome, or to detect epileptic seizures while lying on bed while sleeping or being awake, and all will cause movements of the bed.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

It is a general idea of the invention to use a motion sensor adapted for measuring a movement in a horizontal direction rather than in the vertical direction relative to the ground. This makes no modification of the holder necessary and the force due to the aortic arch impulse is mainly oriented in the horizontal direction while in a direction perpendicular to the horizontal direction, i.e. in the vertical direction relative to the ground, the forces are much smaller.

Figure 1:
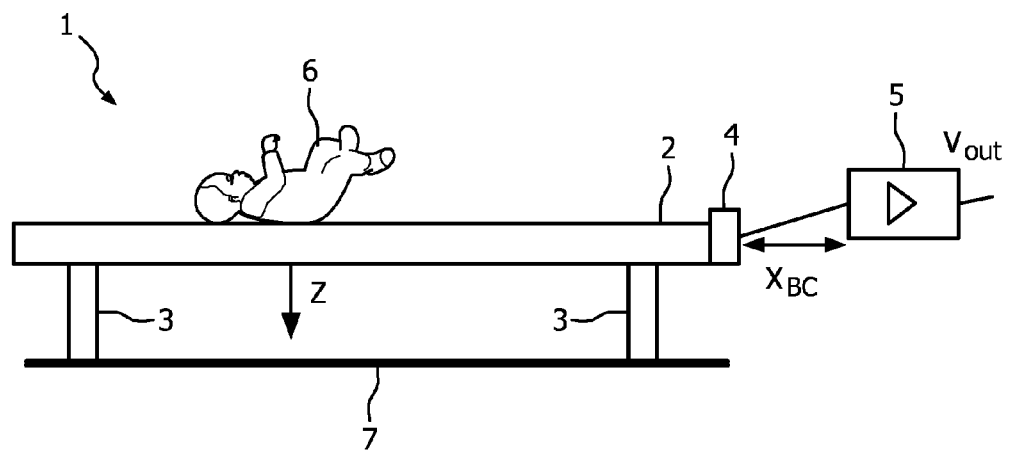
FIG. 1 shows schematically a baby lying on a holder and a measuring system attached to the holder according to a preferred embodiment of the invention.

FIG. 1 schematically shows a baby or neonate 6 lying on a holder 2 operatively connected to a motion sensor 4, wherein the ground 7 is the "fixed world", also referred to as fixed ground. The heart rate measuring apparatus 1 comprises the motion sensor 4 corresponding to an electrical motion sensor according to a preferred embodiment of the invention. The motion sensor 4 comprises a capacitive measuring system which is applied according to the preferred embodiment of the invention. The holder 2 is adapted for carrying the body of the neonate 6 lying on the holder 2, which corresponds to an incubator according to the preferred embodiment of the invention. The holder 2 is adapted for being at least partly moveable in a horizontal direction relative to the ground 7, and the motion sensor 4 is adapted for measuring a signal generated by a movement of the neonate 6 at least partly in the horizontal direction.

According to the preferred embodiment of the invention, the construction of a suspension unit 3 for the holder 2 is such that it can easily be moved in the horizontal direction relative to the ground 7 to a certain amount, such as a few millimeters. Further, an amplifier 5 is used which is adapted for amplifying the signal sensed by the motion sensor 4.

Figure 2:
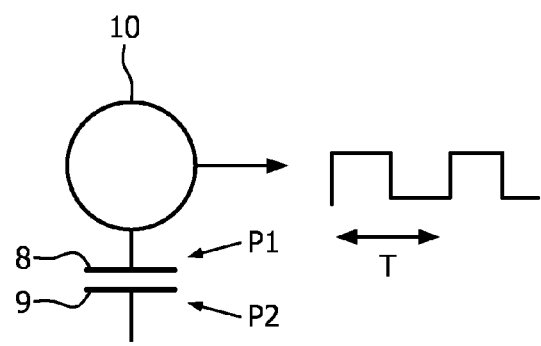
FIG. 2 shows a capacitor comprising an electrical capacitance adapted for determining the oscillating frequency of an oscillator according to a preferred embodiment of the invention.

FIG. 2 shows an arrangement of a measurement system according to a preferred embodiment of the invention. The plates or electrodes 8 and 9, indicated as P1 and P2 in FIG. 2, form a capacitor adapted for determining the oscillating frequency of an oscillator 10, indicated as OSC in FIG. 2, which delivers a signal with an average period time, indicated as T in FIG. 2, modulated with the HR. The first electrode 8 is attached to the fixed ground and the second electrode 9 is attached to the holder 2, as shown in FIG. 1, where the neonate 6 rests on. The oscillator 10 comprises the capacitor with an electrical capacitance depending on predefined parameters, such as the distance between both electrodes 8, 9.

It is worth noting that due to the impulse coursed by the blood flowing through the aortic arch of the neonate 6, the position of the first electrode 8 changes with respect to the second electrode 9 and thus the capacitance changes in value with a rate equal or proportional to the HR or a rate inversely proportional to the average period time T.

Due to the fact that the capacitor formed by the two electrodes 8 and 9 makes part of an oscillator 10, the output signal of the oscillator 10 comprises a signal, wherein the frequency of the signal is modulated with the HR. Assuming that the oscillator's output signal comprises a binary output signal, the output signal is directly in the digital domain and thus must not be converted. However, if the output signal is in the analog domain an ADC is applicable. By detecting the frequency modulation of the signal measured, the ballistographic signal obtained or extracted is used for determining HR or HRV.

According to another preferred embodiment of the invention, the inventive idea is combined with a scale adapted for measuring the force in the vertical direction relative to the ground. Therefore, it becomes not only possible measuring movements in the horizontal direction relative to the ground or relative to the longitudinal direction of the neonate 6 but also measuring the weight of the neonate 6.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A heart rate measuring apparatus, adapted for measuring a subject's heart rate and/or heart rate variation, comprising:
   a holder adapted for carrying at least a portion of a body part of the subject lying on or resting against the holder, and
   a motion sensor operatively connected to the holder,
   wherein the holder is adapted for being at least partly moveable in a horizontal direction relative to the fixed world, and
   the motion sensor is adapted for measuring a signal generated by a movement of the subject at least partly in the horizontal direction relative to the fixed world upon movement of the holder relative to the fixed world, and
   the motion sensor including an electrical motion sensor having a capacitor with an electrical capacitance formed between a first electrode and a second electrode, the first electrode being fixed relative to the fixed world and the second electrode being fixed relative to the holder, at least one of the first and second electrodes being movable relative to the other of the first and second electrodes.

2. The heart rate measuring apparatus according to claim 1, further comprising a monitoring system operatively connected to the motion sensor, wherein the monitoring system is adapted to receive the signal from the motion sensor and is adapted to generate from the signal, information about the subject's heart rate and/or heart rate variation, and is further adapted to relay the information about the subject's heart rate and/or heart rate variation to a user.

3. The heart rate measuring apparatus according to claim 1, wherein the capacitor includes a oscillator circuit, the output of which is a frequency signal modulated by the heart rate.

4. The heart rate measuring apparatus according to claim 1, further comprising a scale adapted for determining the force and/or weight of the subject in a direction at least partly perpendicular to the fixed world.

5. The heart rate measuring apparatus according to claim 1, wherein the holder comprises a suspension structure adapted for allowing a movement of the holder at least partly in the horizontal direction.

6. The heart rate measuring apparatus according to claim 5, wherein the holder comprises a bed, a mattress, a cushion, a crib and/or an incubator.

7. The heart rate measuring apparatus according to claim 5, wherein the suspension structure includes a spring.

8. Use of the heart rate measuring apparatus according to claim 1, wherein the heart rate and/or heart rate variation is adapted to be measured for monitoring applications, and/or the heart rate and/or heart rate variation are used to determine the occurrence of a heart failure, wherein, upon determination of the heart failure, the heart rate measuring apparatus generates an alarm signal.

9. The heart rate measuring apparatus according to claim 1, wherein the first electrode is attached to the fixed world and the second electrode is attached to the holder and spaced from the first electrode, the capacitance of the electrical motion sensor being based on a distance between the first electrode and the second electrode.

10. The heart rate measuring apparatus according to claim 9, wherein the second electrode, attached to the holder, moves relative to the first electrode upon movement of the holder relative to the fixed world.

11. The heart rate measuring apparatus according to claim 10, wherein a change in the distance between the first electrode and the second electrode upon movement of the holder equally or proportionally changes the capacitance of the electrical motion sensor to the heart rate and/or heart rate variation.

12. The heart rate measuring apparatus according to claim 1 wherein:
   the holder is a bed, a mattress, a cushion, a crib or an incubator adapted for the subject to lie horizontally; and
   the motion sensor is adapted to sense the force of the aortic arch impulse of an aorta of the subject in a horizontal direction relative to the ground rather than in the vertical direction using the motion sensor.

13. A method, adapted for measuring a subject's heart rate and/or heart rate variation, comprising:
   operatively connecting a motion sensor to a holder adapted for carrying at least a portion of a body part of the subject lying or resting on the holder;
   moving the holder at least partly in a horizontal direction relative to the fixed world;
   measuring a capacitance signal using of a capacitor including first and second electrodes, the capacitor being associated with the motion sensor to quantify a movement of the subject at least partly in a horizontal direction relative to the fixed world upon movement of the holder relative to the fixed world, at least one of the first and second electrodes being movable relative to the other of the first and second electrodes.

14. The method according to claim 13, further including:
   measuring a capacitance signal using an oscillator circuit associated with the capacitor and outputting-is a frequency signal that is modulated by the heart rate.

15. The method according to claim 13, further including:
   holding at least a portion of a body part of the subject in a suspended manner to allow the horizontal movement of the body part.

16. The method according to claim 13, wherein a movement of the subject in the horizontal direction relative to the fixed world alters a distance between first and second electrodes of the capacitor, thereby altering the capacitance of the capacitor.

17. The method according to claim 13, further including:
relaying information about the subject's heart rate and/or heart rate variation to a user via a monitoring system.

18. The method according to claim 13, wherein a movement of the holder relative to the fixed world moves the second electrode, attached to the holder, relative to the first electrode.

19. The method according to claim 18, wherein a movement of the holder changes a distance between the first electrode and the second electrode, thereby equally or proportionally changing the capacitance of the electrical motion sensor to the heart rate and/or heart rate variation.

20. A heart rate measuring apparatus for measuring a subject's heart rate and/or heart rate variation, comprising:
a holder configured to carry at least a portion of a body part of the subject lying on or resting against the holder, the holder including a suspension member for allowing at least partial movement of the holder in a horizontal direction relative to the fixed world, and
an electrical motion sensor operatively connected to the holder, the electrical motion sensor including a capacitor with an electrical capacitance, the electrical motion sensor including a first plate attached to the fixed world and a second plate attached to the holder and spaced from the first plate such that the second plate is movable relative to the first plate,
wherein the electrical motion sensor is adapted to measure a signal generated by a movement of the subject at least partly in the horizontal direction upon movement of the holder relative to the fixed world.

21. The heart rate measuring apparatus according to claim 20, wherein the capacitance of the electrical motion sensor changes equally or proportionally to the heart rate and/or heart rate variation upon movement of the second plate relative to the first plate.

22. The heart rate measuring apparatus according to claim 20 wherein:
the holder is a bed, a mattress, a cushion, a crib or an incubator adapted for the subject to lie horizontally; and
the electrical motion sensor is adapted to sense the force of the aortic arch impulse of an aorta of the subject in a horizontal direction relative to the ground rather than in the vertical direction using the electrical motion sensor.

* * * * *